US00PP34578P2

(12) United States Plant Patent
Beekenkamp

(10) Patent No.: US PP34,578 P2
(45) Date of Patent: Sep. 13, 2022

(54) ***BEGONIA* PLANT NAMED 'BKPBEEFW'**

(50) Latin Name: ***Begonia* x hiemalis**
Varietal Denomination: BKPBEEFW

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/709,767

(22) Filed: Mar. 31, 2022

(51) Int. Cl.
*A01H 6/18* (2018.01)
*A01H 5/02* (2018.01)

(52) U.S. Cl.
USPC ..... Plt./343

(58) Field of Classification Search
USPC ..... Plt./343
See application file for complete search history.

*Primary Examiner* — Annette H Para
(74) *Attorney, Agent, or Firm* — C. Anne Whealy

(57) ABSTRACT

A new and distinct cultivar of *Begonia* plant named 'BKPBEEFW', characterized by its broadly upright and mounded plant habit; moderately vigorous growth habit; sturdiness; freely basal branching habit; glossy dark green-colored leaves; uniform and freely flowering habit; and double-type flowers that are light yellow green in color.

2 Drawing Sheets

Figure 1:
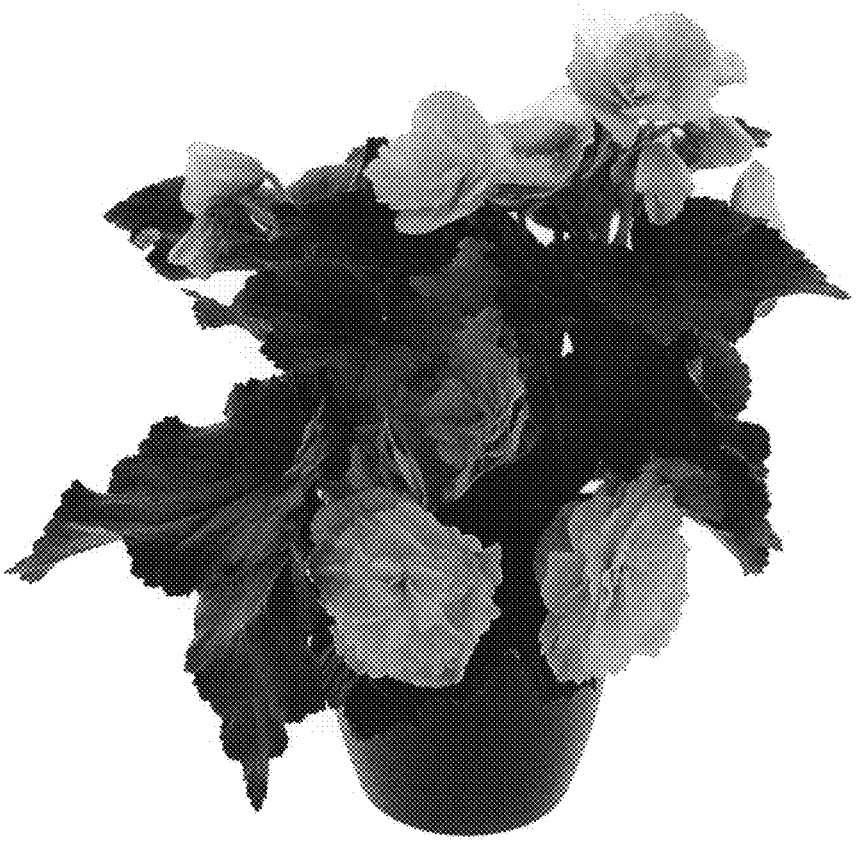

Botanical designation: *Begonia* x *hiemalis*.
Cultivar denomination: 'BKPBEEFW'.

STATEMENT REGARDING PRIOR DISCLOSURES BY THE INVENTOR & APPLICANT/ASSIGNEE

An European Community Plant Breeder's Rights application for the instant plant was filed by the Applicant/Assignee, Beekenkamp Plants B.V. of Maasdijk, The Netherlands on Dec. 23, 2021, application number 2021/3443. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia* x *hiemalis*, commercially referred to as Elatior *Begonia* and hereinafter referred to by the name 'BKPBEEFW'.

The new *Begonia* plant is a product of a planned breeding program conducted by the Inventor in Maasdijk, The Netherlands. The objective of the breeding program was to develop new compact, freely branching and freely flowering *Begonia* plants with attractive flowers and good garden performance.

The new *Begonia* plant is a naturally-occurring whole plant mutation of *Begonia* x *hiemalis* 'BKPBEEFR', disclosed in U.S. Plant Pat. No. 28,684. The new *Begonia* plant was discovered and selected by the Inventor as a single flowering plant from within a population of plants of 'BKPBEEFR' in a controlled greenhouse environment in Maasdijk, The Netherlands in July, 2017.

Asexual reproduction of the new *Begonia* plant by vegetative tip cuttings in a controlled greenhouse environment in Maasdijk, The Netherlands since November, 2017 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEEFW'. These characteristics in combination distinguish 'BKPBEEFW' as a new and distinct *Begonia* plant:

1. Broadly upright and mounded plant habit.
2. Moderately vigorous growth habit.
3. Sturdy plants with freely basal branching habit.
4. Glossy dark green-colored leaves.
5. Uniform and freely flowering habit.
6. Double-type flowers that are light yellow green in color.

Plants of the new *Begonia* can be compared to plants of the mutation parent, 'BKPBEEFR'. Plants of the new *Begonia* differ primarily from plants of 'BKPBEEFR' in flower color as plants of the new *Begonia* have light yellow green-colored flowers whereas plants of 'BKPBEEFR' have pink-colored flowers.

Plants of the new *Begonia* can be compared to plants of *Begonia* x *hiemalis* 'BKPBEEGW', disclosed in U.S. Plant Pat. No. 24,377. Plants of the new *Begonia* differ primarily from plants of 'BKPBEEGW' in plant habit as plants of the new *Begonia* are more freely branching than plants of 'BKPBEEGW'. In addition, plants of the new *Begonia* have larger flowers than plants of 'BKPBEEGW'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) comprises a side perspective view of a typical flowering plant of 'BKPBEEFW' grown in a container.

Figure 2:
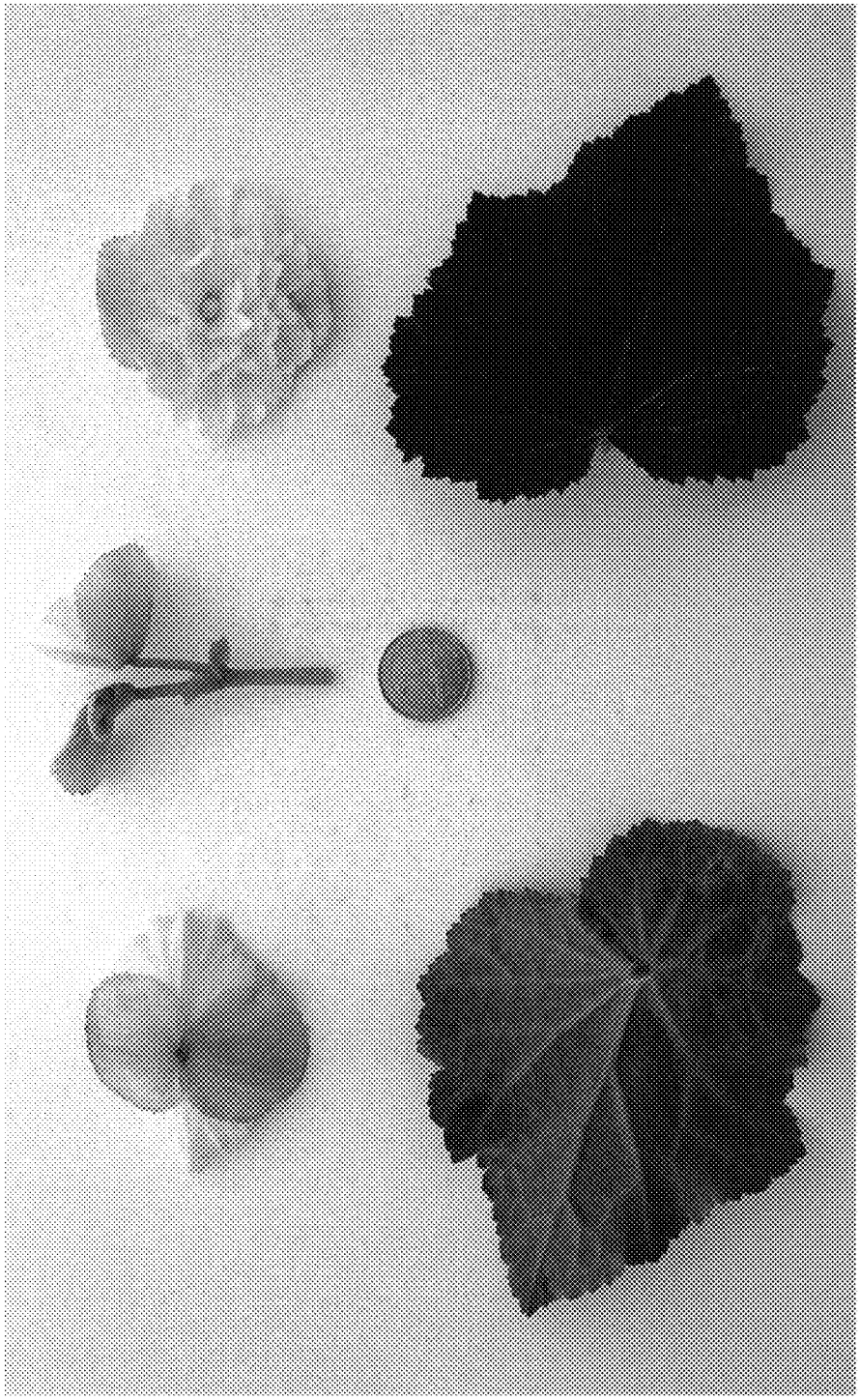

The photograph on the second sheet (FIG. 2) are close-up views of a typical flower bud and the upper and lower surfaces of typical developed flowers and leaves of 'BKPBEEFW'.

DETAILED BOTANICAL DESCRIPTION

Plants used for the aforementioned photographs and following observations and measurements were grown during the autumn in 11-cm containers in a glass-covered greenhouse in Maasdijk, The Netherlands. During the production of the plants, day and night temperatures ranged from 19° to 21° C. Plants were eleven weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia* x *hiemalis* 'BKPBEEFW'.

Parentage: Naturally-occurring whole plant mutation of *Begonia* x *hiemalis* 'BKPBEEFR', disclosed in U.S. Plant Pat. No. 28,684.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically brown in color, actual color of the roots is dependent on substrate composition, water quality, fertilizer type and formulation, substrate temperature and physiological age of roots; to date, plants of the new *Begonia* have not been observed to form tubers.

*Rooting habit*.—Freely branching habit; dense.

Plant description:

*Plant and growth habit*.—Broadly upright and mounded plant habit; overall plant shape, roughly globular; moderately vigorous growth habit and moderate growth rate.

*Plant height, soil level to top of foliar plane*.—About 21.1 cm.

*Plant height, soil level to top of floral plane*.—About 22.7 cm.

*Plant width*.—About 28.4 cm.

*Lateral branch description*.—Branching habit: Freely branching habit with about two basal branches per plant each with about two to three secondary branches; pinching is not required. Length: About 8.2 cm. Diameter: About 8 mm. Internode length: About 2 cm. Strength: Moderately strong. Aspect: About 20° to 40° from vertical. Texture and luster: Sparsely pubescent; slightly velvety; slightly glossy. Color, developing: Close to 146C. Color, fully developed: Close to 146B.

*Leaf description*.—Arrangement: Alternate, simple. Length: About 14.4 cm. Width: About 10.6 cm. Shape: Broadly ovate, unequal. Apex: Acute. Base: Oblique, lobes slightly imbricate. Margin: Serrate to dentate; slightly to moderately undulate. Texture and luster, upper surface: Smooth, glabrous; velvety; moderately glossy. Texture and luster, lower surface: Mostly smooth and glabrous with sparse pubescence along the veins; velvety; slightly glossy. Venation pattern: Pinnate. Color: Developing leaves, upper surface: Close to 199A. Developing leaves, lower surface: Close to 183C. Fully expanded leaves, upper surface: Darker than a blend of 139A and N189A; venation, close to 138A. Fully expanded leaves, lower surface: Close to 191B slightly to strongly tinged with close to 183C; venation, close to 146B. Petioles: Length: About 4.7 cm. Diameter: About 6 mm. Strength: Flexible. Texture and luster, upper and lower surfaces: Sparsely to moderately pubescent; slightly glossy. Color, upper surface: Close to 146C; at distal end, tinged with close to 181B and at proximal end, slightly tinged with close to 173A. Color, lower surface: Close to 146C. Stipules: Quantity per leaf: Two at the base of the leaf. Length: About 1.1 cm. Width: About 1.2 cm. Shape: Broadly ovate. Apex: Obtuse. Base: Broadly cuneate. Margins: Ciliate. Color, upper and lower surfaces: Close to 145A.

Flower description:

*Flowering habit*.—Rotate double-type sterile male flowers arranged in axillary compound cymes; freely flowering habit with about four flowers per cyme and about 140 flowers developing per plant during the flowering season; flowers face upright to outwardly.

*Fragrance*.—None detected.

*Natural flowering season*.—Long flowering period, plants flower freely and continuously from spring into the autumn in The Netherlands; during the winter in a greenhouse, plants begin flowering about 45 days after exposure to photoinductive treatments.

*Postproduction longevity*.—Individual flowers last about ten days on the plant; flowers not persistent; flowering plants maintain good substance for about 20 to 30 days in an interior environment.

*Inflorescence height*.—About 12.3 cm.

*Inflorescence diameter*.—About 10 cm.

*Flower buds*.—Length: About 2 cm. Diameter, flattened: About 0.7 cm to 2.2 cm. Shape: Broadly obovate to flabellate; flattened. Texture and luster: Smooth, glabrous; slightly velvety; matte. Color: Close to 145B; distally, close to 145C; at the margins, slightly tinged with close to 181D.

*Flowers*.—Diameter: About 6.8 cm. Depth: About 2.6 cm. Tepals: Quantity and arrangement: Four per flower arranged in two whorls. Length, lower whorl: About 3.8 cm. Width, lower whorl: About 4 cm. Length, upper whorl: About 3.9 cm. Width, upper whorl: About 3.9 cm. Shape: Nearly orbicular. Apex, lower whorl: Obtuse to shallowly praemorse. Apex, upper whorl: Bluntly acute to shallowly praemorse. Base, lower whorl: Truncate. Base, upper whorl:

Cuneate. Margin: Entire, not undulate. Texture and luster, lower and upper whorls, upper surface: Smooth, glabrous, velvety; matte. Texture and luster, lower whorl, lower surface: Smooth, glabrous, moderately velvety; slightly glossy. Texture and luster, upper whorl, lower surface: Smooth, glabrous, moderately velvety; matte. Color, lower whorl: When opening, upper surface: Close to 145D. When opening, lower surface: Close to a blend of 145D and 150D; towards the base, close to 145A; and towards the apex and margins, slightly tinged with close to 181D. Fully opened, upper surface: Close to 145D; towards the apex and margins, slightly tinged with close to 144A and 182D; venation, similar to lamina colors; color does not fade with development. Fully opened, lower surface: Close to 145A; towards the apex and margins, moderately to strongly tinged with close to 179C and 180C; venation, similar to lamina colors; color does not fade with development. Color, upper whorl: When opening, upper surface: Close to 157B; towards the base, close to 145A. When opening, lower surface: Close to 157A to 157B; towards the base, close to 145A. Fully opened, upper surface: Close to 157B; towards the apex, close to 157A; venation, slightly lighter than 147D; color does not fade with development. Fully opened, lower surface: Close to 157B; towards the apex, close to 157A; venation, close to 147D; color does not fade with development. Tepaloids: Quantity and arrangement: About 30 arranged in about seven whorls interior to the tepals. Length: About 2.9 cm, varying between 1.2 cm and 3.9 cm. Width: About 2.4 cm, varying between 0.9 cm and 3.3 cm. Shape: Obovate. Apex: Coarsely praemorse with obtuse, bluntly acute and/or acute lobe apices. Base: Cuneate. Margin: Entire, not undulate. Texture and luster, upper surface: Smooth, glabrous, slightly velvety; matte. Texture and luster, lower surface: Smooth, glabrous, moderately velvety; matte. Color: When opening, upper surface: Close to 157B; towards the base, close to 157A. When opening, lower surface: Close to 157B; towards the base, close to a blend of 145D and 157A. Fully opened, upper surface: Close to 157B; towards the apex, close to 157A; venation, lighter than 146D; color does not fade with development. Fully opened, lower surface: Close to 157B to 157C; towards the apex, close to 157A to 157B; venation, lighter than 146D; color does not fade with development.

*Peduncles*.—Length: About 11.5 cm. Diameter: About 5.5 mm. Angle: About 30° from lateral branch axis. Strength: Moderately strong; flexible. Texture and luster: Sparsely pubescent; moderately glossy. Color: Close to 146B and 146C.

*Pedicels*.—Length: About 2.9 cm. Diameter: About 3.5 mm. Angle: About 30° from the peduncle axis. Strength: Moderately strong; flexible. Texture and luster: Smooth, glabrous; moderately glossy. Color: Close to 144A to 144B.

*Flower bracts*.—Quantity and arrangement: Two per flower, opposite. Length: About 1 cm. Width: About 1.4 cm. Shape: Reniform, concave. Apex: Bluntly acute. Base: Broadly cuneate. Margin: Ciliate. Texture and luster, upper and lower surfaces: Smooth, glabrous; slightly velvety; very slightly glossy. Color, upper and lower surfaces: Close to 144B; towards the base, close to 144A.

*Reproductive organs*.—None observed, all structures transformed into tepaloids.

*Seeds and fruits*.—Seed and fruit development have not been observed on plants of the new *Begonia* as flowers are sterile.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKP-BEEFW' as illustrated and described.

* * * * *